(12) United States Patent
Miyamura et al.

(10) Patent No.: US 10,086,101 B2
(45) Date of Patent: Oct. 2, 2018

(54) DEODORANT, DEODORANT COMPOSITION, AND DEODORIZING PRODUCT

(71) Applicant: TOAGOSEI CO., LTD., Tokyo (JP)

(72) Inventors: Kentaro Miyamura, Nagoya (JP); Koji Sugiura, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 0 days.

(21) Appl. No.: 15/535,807

(22) PCT Filed: Oct. 28, 2015

(86) PCT No.: PCT/JP2015/080370
§ 371 (c)(1),
(2) Date: Jun. 14, 2017

(87) PCT Pub. No.: WO2016/098461
PCT Pub. Date: Jun. 23, 2016

(65) Prior Publication Data
US 2017/0333588 A1    Nov. 23, 2017

(30) Foreign Application Priority Data
Dec. 19, 2014   (JP) .................. 2014-257087

(51) Int. Cl.
| | |
|---|---|
| *A61L 9/01* | (2006.01) |
| *B01J 20/02* | (2006.01) |
| *C01B 33/20* | (2006.01) |
| *B01J 20/10* | (2006.01) |

(52) U.S. Cl.
CPC ............ *A61L 9/01* (2013.01); *B01J 20/0237* (2013.01); *B01J 20/10* (2013.01); *C01B 33/20* (2013.01)

(58) Field of Classification Search
CPC ....................................................... A61L 9/01
See application file for complete search history.

(56) References Cited

U.S. PATENT DOCUMENTS

| 5,559,070 A | 9/1996 | Torii et al. |
| 2004/0120921 A1 | 6/2004 | Quincy, III et al. |
| 2004/0217061 A1 | 11/2004 | Corzani et al. |

FOREIGN PATENT DOCUMENTS

| JP | 1-223968 A | 9/1989 |
| JP | 2-265644 A | 10/1990 |
| JP | 4-290546 A | 10/1992 |
| JP | 6-305724 A | 11/1994 |
| JP | 8-283013 A | 10/1996 |
| JP | 10-155883 A | 6/1998 |
| JP | 2003-052800 A | 2/2003 |
| JP | 2005-087630 A | 4/2005 |
| JP | 2005-510339 A | 4/2005 |
| JP | 2006-511338 A | 4/2006 |
| JP | 2011-104274 A | 6/2011 |

OTHER PUBLICATIONS

Brandao, P. et al., "A novel microporous copper silicate:Na2Cu2Si4O11. 2H2O", Chem. Communication 2005, 171-173.*
International Search Report (PCT/ISA/210) issued in PCT/JP2015/080370, dated Jan. 19, 2016.
Written Opinion (PCT/ISA/237) issued in PCT/JP2015/060370, dated Jan. 19, 2016.

* cited by examiner

*Primary Examiner* — Gina C Justice
(74) *Attorney, Agent, or Firm* — Birch, Stewart, Kolasch & Birch, LLP

(57) ABSTRACT

It is an object of the present invention to provide a deodorant or a deodorant composition which has excellent deodorizing performance with respect to sulfurous stench from methyl mercaptan and hydrogen sulfide and the like. It is another object of the present invention to provide a deodorant or a deodorant composition which maintains a deodorizing effect with respect to sulfurous stench and which makes it possible to suppress resin deterioration in the case of being kneaded into a resin, and a deodorizing product containing the same. A deodorant of the present invention contains amorphous copper silicate represented by the following formula [1]:

$x\text{Na}_2\text{O} \cdot y\text{CuO} \cdot \text{SiO}_2 \cdot z\text{H}_2\text{O}$   [1]

wherein, in formula [1], x is a positive number from 0.002 to 0.040, y is a positive number from 0.07 to 0.48, and z is a positive number from 0.02 to 0.30.

5 Claims, No Drawings

DEODORANT, DEODORANT COMPOSITION, AND DEODORIZING PRODUCT

CROSS-REFERENCE TO RELATED APPLICATIONS

This application is the National Phase of PCT International Application No. PCT/JP2015/080370, filed on Oct. 28, 2015, which claims priority under 35 U.S.C. 119(a) to Patent Application No. 2014-257087, filed in Japan on Dec. 19, 2014, all of which are hereby expressly incorporated by reference into the present application.

All publications, patent applications, and technical standards mentioned in this specification are herein incorporated by reference to the same extent as if each individual publication, patent application, or technical standard was specifically and individually indicated to be incorporated by reference.

TECHNICAL FIELD

The present invention relates to a deodorant, a deodorant composition, and a deodorizing product containing the same. Furthermore, in particular, the present invention relates to a deodorant having excellent deodorizing performance with respect to sulfurous stench and a deodorizing product containing the deodorant.

BACKGROUND ART

In recent years, demands for a comfortable life have been rapidly increasing, and a deodorizing product capable of removing personal stench highly have attracted attention as one of them. Particularly, sulfurous stench which contains a compound containing a sulfur element such as methyl mercaptan or hydrogen sulfide as a main component is disliked because the sulfurous stench applies strong displeasure. A deodorant effective for these sulfurous stenches has been desired. However, activated carbon, activated carbon impregnated with an aromatic primary amine, activated carbon having adjusted pH, any combination of an iron compound and ascorbic acid, and a polymer compound having an amino group or a sulfone group, and the like which are conventionally known general deodorants, have low sulfurous stench deodorizing capability. These deodorants may be originally colored, or may adsorb stench components or be subjected to a chemical reaction to cause coloration or discoloration. Disadvantageously, the deodorants could not be used depending on the application.

On the other hand, a deodorant containing a hydroxide or a hydrous oxide of a zirconium or lanthanoid element as an active ingredient is reported as a deodorant having a deodorization function with respect to sulfurous stench in Patent Document 1. A sulfurous stench gas deodorant containing a quadrivalent metal phosphate containing specific metal ions is proposed in Patent Document 2. Furthermore, a deodorant containing specific fine particle zinc oxide and having high deodorizing performance with respect to hydrogen sulfide is shown in Patent Document 3.

Consideration is also performed in order to improve the deodorizing properties of methyl mercaptan. For example, a stench gas adsorbent having a metal salt contained in a silica gel structure is proposed in Patent Document 4. A sulfur-based gas deodorant which is an amorphous complex of a specific metal salt and silicate salt, and has a pore volume of from 0.3 to 0.5 ml/g is proposed in Patent Document 5, and the molar ratio of the metal salt and silicate salt in a case in which the deodorant is manufactured is from 0.29 to less than 0.5. Furthermore, a sulfur-based gas deodorant containing an amorphous metal silicate salt is proposed in Patent Document 6. In the amorphous metal silicate salt, the element composition (mole) ratio of at least one metal selected from copper, zinc, manganese, cobalt, and nickel to silicon is within the range of metal/silicon=0.60 to 0.80, and a crush strength is within the range of from 1 to 3 N.

PRIOR ART DOCUMENTS

Patent Documents

Patent Document 1: JP-A-01-223968 (JP-A denotes a Japanese unexamined patent application publication)
Patent Document 2: JP-A-10-155883
Patent Document 3: JP-A-2003-52800
Patent Document 4: JP-A-04-290546
Patent Document 5: JP-A-2005-87630
Patent Document 6: JP-A-2011-104274

SUMMARY OF THE INVENTION

Problems to be Solved by the Invention

However, the deodorants disclosed in Patent Documents 1 to 3 have disadvantageously insufficient deodorizing performance with respect to sulfurous stench, and particularly methyl mercaptan. Although the deodorants disclosed in Patent Documents 4 to 6 have an excellent deodorizing effect with respect to sulfurous stench, the deterioration of a resin is caused by copper ions in a case in which the deodorants are kneaded in the resin, which causes the discoloration and abnormal odor of a resin product. This disadvantageously limits applications and processing conditions. The deterioration of the resin caused by the copper ions is so-called copper damage, which notably appears during processing involving heating. Specifically, a plate obtained by melt-forming a resin-molded product at 220° C. has dark green, and releases abnormal odor. The resin-molded product is obtained by blending 10% of a copper silicate deodorant containing copper in high concentration so that the molar ratio of $CuO/SiO_2$ is 0.55 with a forming polypropylene resin. In a case in which a sensory test according to olfaction is performed using a clothing fabric obtained by subjecting an acrylic emulsion blended so that the ratio of resin solid content:deodorant is 1:1 (mass ratio) to spreading processing of 5 g/m$^2$, clear abnormal odor may be felt.

The present invention has been made in view of the above-mentioned problems, and it is an object of the present invention to provide a deodorant or a deodorant composition which has excellent deodorizing performance with respect to sulfurous stench from methyl mercaptan and hydrogen sulfide and the like. It is another object of the present invention to provide a deodorant or a deodorant composition which maintains a deodorizing effect with respect to sulfurous stench and which makes it possible to suppress resin deterioration in the case of being kneaded into a resin, and a deodorizing product containing the same.

Means for Solving the Problems

The present inventors earnestly worked on the conventional problems, and found that amorphous copper silicate having a specific composition exhibited excellent deodorizing performance with respect to sulfurous stench. Therefore, the invention has been completed. That is, the present invention is as follows.

1. A deodorant containing amorphous copper silicate represented by the following formula [1]:

$$x\text{Na}_2\text{O}\cdot y\text{CuO}\cdot\text{SiO}_2\cdot z\text{H}_2\text{O} \qquad [1]$$

wherein, in formula [1], x is a positive number from 0.002 to 0.040, y is a positive number from 0.07 to 0.48, and z is a positive number from 0.02 to 0.30.

2. The deodorant according to the above 1, wherein the amorphous copper silicate has a bulk specific gravity of from 0.10 to 0.40 g/ml.

3. A deodorant composition containing the deodorant according to the above 1 or 2.

4. A deodorizing product containing the deodorant according to the above 1 or 2 or the deodorant composition according to the above 3.

Effects of the Invention

The present invention can provide a deodorant or a deodorant composition which has excellent deodorizing performance with respect to sulfurous stench from methyl mercaptan and hydrogen sulfide and the like. The present invention can provide a deodorant or a deodorant composition which maintains a deodorizing effect with respect to sulfurous stench and which makes it possible to suppress resin deterioration in the case of being kneaded into a resin, and a deodorizing product containing the same.

MODE FOR CARRYING OUT THE INVENTION

An embodiment of the present invention will be described as follows, but the present invention is not limited thereto. "%" indicates % by mass, and "part(s)" indicates part(s) by mass unless otherwise specified.

In the present invention, the description of "from lower limit to upper limit" representing a numerical value range represents "lower limit or more and upper limit or less", and the description of "from upper limit to lower limit" represents "upper limit or less and lower limit or more". That is, the description of "from lower limit to upper limit" represents a numerical value range including the upper limit and the lower limit.

In the present invention, any combination of two or more preferable aspects is a more preferable aspect.

1. Deodorant

Since a deodorant of the present invention has a deodorizing effect with respect to sulfurous stench from methyl mercaptan and hydrogen sulfide and the like, the deodorant can exclude various odors occurring in living environments such as stool odor, life odor, and kitchen garbage odor.

The deodorant of the present invention is a deodorant containing amorphous copper silicate represented by the following formula [1]:

$$x\text{Na}_2\text{O}\cdot y\text{CuO}\cdot\text{SiO}_2\cdot z\text{H}_2\text{O} \qquad [1]$$

wherein, in formula [1], x is a positive number from 0.002 to 0.040, y is a positive number from 0.07 to 0.48, and z is a positive number from 0.02 to 0.30.

The value of x may influence resin deterioration. In a case in which the value exceeds 0.040, the resin deterioration remarkably proceeds, which influences the appearance of a deodorizing product, and the like. Also, in a case in which the value of x is less than 0.002, the resin deterioration is not effectively suppressed, which tends to cause deterioration in deodorizing performance. The range of x is preferably from 0.002 to 0.035, and more preferably from 0.002 to 0.030.

The value of y influences the deodorizing effect and the resin deterioration. In a case in which the value is less than 0.07, a sufficient deodorizing effect is not obtained. In a case in which the value of y exceeds 0.48, improvement in the deodorizing effect cannot be expected, which tends to make the resin deterioration also proceed. The value of y is preferably from 0.10 to 0.43, and more preferably from 0.15 to 0.38.

The value of z may influence the resin deterioration. In a case in which the value is less than 0.02, the deodorant is apt to absorb moisture, which causes difficult handling. In a case in which the value exceeds 0.30, poor forming such as foaming or silver streak is apt to be caused in a case in which the resin is molded. The range of z is preferably from 0.05 to 0.25, and more preferably from 0.10 to 0.20.

The amorphous copper silicate used for the present invention preferably has an extremely high bulk specific gravity of from 0.10 to 0.40 g/ml. While the high bulk specific gravity reduces a contact area with the resin, the high bulk specific gravity is a factor which can exhibit high deodorizing properties. In a case in which the bulk specific gravity is 0.40 g/ml or less, the resin deterioration can be sufficiently suppressed. In a case in which the bulk specific gravity is 0.10 g/ml or more, the amorphous copper silicate is likely to practically handled, and is easily kneaded in the resin. The bulk specific gravity is more preferably from 0.12 to 0.35 g/ml, and still more preferably from 0.15 to 0.30 g/ml.

That is, in a case in which the bulk specific gravity of the amorphous copper silicate is within the above range, discoloration and abnormal odor in a case in which the deodorant is applied to the resin or kneaded in the resin are decreased, and thereby the amorphous copper silicate can be used for various deodorizing products.

The amorphous copper silicate of the present invention can be manufactured in a state where the molar ratio of a copper salt and silicate salt is from 0.07 to 0.48. Copper sulfate, copper chloride, and copper acetate and the like can be used for the raw materials of the copper salt. Liquid glass, alkaline silicate, and colloidal silica can be used for the raw materials of the silicate salt. The pH of an aqueous solution in which a copper salt is dissolved is preferably adjusted to 0 to 2 by adding sulfuric acid to the aqueous solution. The copper salt aqueous solution and the silicate salt aqueous solution are mixed in a solution state and reacted with each other under a condition where the pH does not depart from the range of from 6.0 to 9.0, to obtain the amorphous copper silicate. The pH of the reaction liquid in which the copper salt and the silicate salt coexist is more preferably within the range of from 6.0 to 7.5, and still more preferably from 6.5 to 7.0. In order to keep the pH of the copper salt which is an acidic solution and the silicate salt which is an alkaline solution during an instillation reaction at 6.0 to 9.0, both the raw materials are preferably subjected to simultaneous instillation from the time of instillation start. It is preferable that the pH of the reaction liquid is measured if appropriate to adjust the instillation speeds of the copper salt and silicate salt. Since a slow initial instillation speed is likely to respond to a rapid change in the pH, the copper salt and the silicate salt are preferably prepared at such an instillation speed that a time until the instillation of all the raw materials is completed is 30 minutes or more, and preferably 1 hour or more.

Since a temperature in a case in which the amorphous copper silicate is manufactured influences the performance of the deodorant, the temperature is preferably within the range of from 5 to 50° C., and more preferably within the range of from 10 to 40° C. Since the reaction is not completely completed immediately after the instillation of the raw materials, continuous stirring is preferably performed for preferably 10 minutes to 24 hours immediately after the preparation of the raw materials, and more preferably for about 1 to about 12 hours.

In a case in which the amorphous copper silicate is manufactured, a by-product salt is produced. If the salt remains in a significant amount in the deodorant, the resin deterioration is promoted in a case in which the deodorant is blended with the resin. Therefore, water washing makes it necessary to remove the salt. However, excessive water washing tends to cause the deterioration in the deodorizing performance. Therefore, a slurry after manufacturing is preferably washed with water so that the electrical conductivity of a filtrate after water washing is from 5 to 200 µS/cm, and preferably from 5 to 50 µS/cm.

The amorphous copper silicate which is the deodorant of the present invention is an amorphous complex of the copper salt and silicate salt, and is a powder having a light blue or blue appearance color. Since a deep appearance color influences a color change in a product, the appearance color is preferably dilute. A specific color preferably has an L value of 80 or more, a value of −13 or more, and a b value of −15 or more in Lab view. The BET specific surface area of the amorphous copper silicate of the present invention is a large specific surface area of from 300 to 550 $m^2/g$. A large BET specific surface area is an important requirement for improving the deodorizing performance of the deodorant, and preferably from 350 to 550 $m^2/g$, and more preferably from 380 to 500 $m^2/g$. Since the amorphous copper silicate has an amorphous structure, a crystal peak is not detected in powder XRD diffraction. The particle diameter of the amorphous copper silicate of the present invention is from 1 µm to several millimeters. It is necessary to carry out jet mill pulverization and the like in order to obtain the amorphous copper silicate having a median size of 30 µm or less. In order to apply the amorphous copper silicate to various products, the amorphous copper silicate preferably has a smaller particle diameter. The amorphous copper silicate preferably has a median size of 10 µm or less. The lower limit of the median size is preferably 50 nm or more without particular limitation.

The deodorizing performance of the deodorant can be represented by a deodorization capacity with respect to sulfurous stench. Examples of the sulfurous stench include methyl mercaptan, hydrogen sulfide, dimethyl sulfide, and methyl disulfide. In particular, methyl mercaptan and hydrogen sulfide are typical sulfurous stenches.

The deodorization capacity is represented by the gas volume of stench which can be absorbed to 1 g of the deodorant. The deodorization capacity of hydrogen sulfide provided by the deodorant of the present invention is 80 ml/g or more, and preferably is 100 ml/g or more. The upper limit is preferably higher without particular limitation, and realistically 5,000 ml/g or less.

The deodorization capacity of methyl mercaptan is 20 ml/g or more, and preferably 30 ml/g or more. The upper limit is preferably higher without particular limitation, and realistically 5,000 ml/g or less.

In a case in which the deodorization capacity of hydrogen sulfide is less than 80 ml/g or the deodorization capacity of methyl mercaptan is less than 20 ml/g, good processability and less resin deterioration are provided, but an excellent deodorizing effect is not exhibited, which causes extremely low effectivity as a sulfurous stench deodorant.

2. Deodorant Composition

In order to efficiently remove composite type stench in which several sorts of stench sources containing sulfurous stench are mixed, a mixture containing the deodorant of the present invention and a known deodorant can be used as the deodorant composition, or the deodorant of the present invention and the known deodorant can be used in combination. Examples of the known deodorant include at least one deodorant selected from the group consisting of an acidic gas deodorant, a basic gas deodorant, and an aldehyde-based gas deodorant. Specific examples thereof include activated carbon, zeolite, silica gel, aluminum silicate, hydrous zirconium oxide, zirconium phosphate, zinc oxide, aluminum oxide, and sepiolite.

3. Deodorizing Product

The deodorant and deodorant composition of the present invention can be used as a final deodorizing product placed in a container such as a cartridge as it is in a powder or granule form. The effects of the deodorant and deodorant composition can be exhibited by leaving the deodorant and the deodorant composition near a stench generation source inside and outside a room, and the like. Furthermore, as described in full detail below, the deodorant and deodorant composition of the present invention are blended with a fiber, a coating material, a sheet, or a resin molded product and the like, and can be utilized in order to manufacture a deodorizing product.

Examples of the deodorizing product of the present invention include a deodorizing fiber, a deodorizing coating material, a deodorizing sheet, and a deodorizing resin molded product.

(1) Deodorizing Fiber

One of useful deodorizing products using the deodorant or deodorant composition of the present invention is the deodorizing fiber. In this case, a raw fiber may be a natural fiber or a synthetic fiber. The raw fiber may be a short fiber, a long fiber, or a composite fiber having a core-clad structure, and the like.

A method of applying deodorizing performance to a fiber using the deodorant of the present invention is not particularly limited. For example, in a case in which the deodorant of the present invention is applied to the fiber during post-processing, the surface of the fiber can be coated with the deodorant by adhering a deodorant-containing water-based or organic solvent-based suspension to the surface of the fiber according to a method such as applying or dipping, and removing a solvent. In order to increase an adhesion force with respect to the surface of the fiber, a binder may be added to the suspension, followed by mixing. The pH of the deodorant-containing water-based suspension is not particularly limited, but the pH is preferably from about 6 to about 8 in order to sufficiently exhibit the performance of the deodorant.

By kneading the deodorant of the present invention in a molten liquid fiber resin or a dissolved fiber resin solution to produce a kneaded product, and fiberizing the kneaded product, a fiber having deodorizing performance can be obtained. Any known chemical fibers can be used as the fiber resin which can be used by the method. Examples of the fiber resin include polyester, nylon, acrylic, polyethylene, polyvinyl, polyvinylidene, polyurethane, and polystyrene. These resins may be a homopolymer or a copolymer. In the case of the copolymer, the polymerization proportion of each copolymer component is not particularly limited.

The proportion of the deodorant of the present invention contained in the fiber resin is not particularly limited. In a case in which the content of the deodorant is generally increased, deodorizing properties can be strongly exhibit, and can be maintained for a long period of time. However, even if the deodorant is contained in an amount which is equal to or greater than a certain level, no large difference may occur in a deodorizing effect, or the strength of the fiber may be decreased. Therefore, the proportion of the deodorant is preferably from 0.1 to 20 parts by mass, and more preferably from 0.5 to 10 parts by mass based on 100 parts by mass of the fiber resin. The deodorizing fiber containing the deodorant of the present invention can be utilized in various fields where deodorizing properties are required. For example, the deodorizing fiber may be used in many fiber products including underclothings, stockings, socks, duvets, duvet covers, cushions, blankets, carpets, curtains, sofas, car seats, air filters, and care clothes.

(2) Deodorizing Coating Material

Another deodorizing product of the useful deodorizing products containing the deodorant or deodorant composition of the present invention is the deodorizing coating material. In a case in which the deodorizing coating material is manufactured, fat and oil, or a resin serving as the main component of a coating material vehicle to be used may be any of natural vegetable oil, a natural resin, a semisynthetic resin, and a synthetic resin, or any of a thermoplastic resin and a thermosetting resin without particular limitation. Examples of the fat and oil and the resin which can be used include drying oil or semidrying oil such as flaxseed oil, chinese tung oil, or soybean oil, rosin, nitrocellulose, ethyl cellulose, cellulose acetate butyrate, benzylcellulose, a novolac type or resol type phenol resin, an alkyd resin, an amino alkyd resin, an acrylic resin, vinyl chloride, a silicone resin, a fluorine resin, an epoxy resin, an urethane resin, a saturated polyester resin, a melamine resin, and a polyvinylidene chloride resin.

The deodorant of the present invention can be used for both a liquid coating material and a powder coating material. The deodorizing coating material containing the deodorant of the present invention may be cured according to any mechanism. Specific examples of the deodorizing coating material include an oxidation polymerization type, a humidity polymerization type, a heating curing type, a catalyst curing type, an ultraviolet curing type, and a polyol curing type. A pigment, a dispersing agent, and other additive agent used in the deodorizing coating material are not particularly limited except for those which may cause a chemical reaction with amorphous copper silicate or a deodorizing substance used together with the amorphous copper silicate. The deodorizing coating material containing the deodorant or deodorant composition of the present invention can be easily prepared. Specifically, the deodorant and the coating material component may be sufficiently dispersed and mixed using a general mixing device such as a ball mill, a roll mill, a disper, or a mixer.

The proportion of the deodorant of the present invention contained in the deodorizing coating material is not particularly limited. In a case in which the content of the deodorant is generally increased, deodorizing properties can be strongly exhibit, and can be maintained for a long period of time. However, even if the deodorant is contained in an amount which is equal to or greater than a certain level, no large difference may occur in a deodorizing effect, or the glazing of the surface to be coated is lost or cracks occur. Thereby, the proportion of the deodorant is preferably from 0.1 to 20 parts by mass, and more preferably from 0.5 to 10 parts by mass based on 100 parts by mass of the coating material composition.

The deodorizing coating material containing the deodorant of the present invention can be utilized in various fields where deodorizing properties are required. For example, the deodorizing coating material can be used for internal walls and external walls for buildings, vehicles, and railroads and the like, garbage incinerator plant facilities, and a kitchen garbage container and the like.

(3) Deodorizing Sheet

Another deodorizing product of the useful deodorizing products containing the deodorant or deodorant composition of the present invention is the deodorizing sheet. The material and fine structure and the like of a sheet material used as a raw material are not limited. The material is preferably a resin, paper, or a composite thereof. The material is preferably a porous material. Preferable specific examples of the sheet material include Japanese paper, synthetic paper, a nonwoven fabric, and a resin film. The sheet material is particularly preferably paper made of natural pulp and/or synthetic pulp. In a case in which the natural pulp is used, a deodorant particle powder is inserted between the finely branched fibers, which advantageously provides a practical support body without particularly using a binding material. The synthetic pulp advantageously has excellent chemical resistance. In a case in which the synthetic pulp is used, the insertion of the powder between the fibers may become difficult to support the deodorant particles. Thereby, a part of the fibers may be melted to increase an adhesion force between the powder and the fiber in a drying process after paper making, or another thermosetting resin fiber may be mixed in a part of the fibers. Thus, in a case in which the natural pulp and the synthetic pulp are mixed and used in a proper proportion, paper having adjusted various characteristics can be obtained. In a case in which the proportion of the synthetic pulp is generally increased, paper having excellent strength, water resistance, chemical resistance, and oil resistance and the like can be obtained.

In a case in which the proportion of the natural pulp is increased, paper having excellent water absorbability, gas permeability, hydrophilicity, forming processability, and drape and the like can be obtained.

A method of supporting the deodorant of the present invention on a sheet material is not particularly limited. The deodorant of the present invention may be supported when or after a sheet is manufactured. For example, in a case in which the deodorant is supported on paper, the deodorant is optionally introduced in the paper-making process, or a liquid in which the deodorant is dispersed is applied, immersed, or sprayed on previously manufactured paper together with a binder. Hereinafter, a method of introducing the deodorant of the present invention in a paper-making process will be described as an example. The paper-making process itself may be performed according to a known method. For example, first, an aggregate is produced by adding 5% by mass or less of a cationic flocculant and 5% by mass or less of an anionic flocculant to a slurry containing a deodorant and pulp in predetermined proportion. Then, the aggregate is subjected to paper making according to a known method, and is dried at a temperature of from 100 to 190° C., thereby obtaining paper on which the deodorant is supported.

In a case in which the amount of the deodorant of the present invention supported on the sheet material is generally increased, deodorizing properties can be strongly exhibited, and can be maintained for a long period of time. However, even if the deodorant is supported in an amount which is equal to or greater than a certain level, a deodorizing effect is not largely changed. Therefore, in a case where the deodorant is supported on the surface and entire inside of the sheet during the paper-making process, the supported amount of the deodorant is preferably from 0.1 to 10 parts by mass based on 100 parts by mass of the sheet. In a case where the deodorant is supported on only the surface of the sheet during post-processing by coating and the like, the supported amount of the deodorant is from 0.05 to 10 g/m².

The deodorizing sheet containing the deodorant of the present invention may be utilized in various types of fields where deodorizing properties are required. For example, the deodorizing sheet may be used as medical packaging paper, food packaging paper, electrical instrument packaging paper, a care paper product, freshness-retaining paper, clothing made of paper, an air cleaner filter, wall paper, tissue paper, and toilet paper and the like.

(4) Deodorizing Resin Molded Product

Examples of the application of the deodorant of the present invention include the application of the deodorant to the deodorizing resin molded product. In a case in which the deodorant of the present invention is added to the resin, it is also possible to mix the resin and the deodorant as it is, and to introduce the mixture to a molding machine where the mixture is molded, and it is also possible to previously prepare a pellet type resin containing the deodorant in high concentration, and to mix the pellet type resin with a main resin, followed by molding. In order to improve physical properties, if necessary, other various additive agents such as a pigment, a dye, an antioxidant, a light resistance stabilizing agent, an antistatic agent, a foaming agent, an impact resistance strengthening agent, a glass fiber, a moisture-proof agent, and an extender can also be blended with the resin.

The proportion of the deodorant of the present invention contained in the deodorizing resin molded product is not particularly limited. If the content of the deodorant is generally increased, deodorizing properties can be strongly exhibited, and can be maintained for a long period of time. However, even if the deodorant is contained in an amount which is equal to or greater than a certain level, no large difference may occur in a deodorizing effect. Thereby, the content of the deodorant is preferably from 0.1 to 30 parts by mass, and more preferably from 0.5 to 25 parts by mass based on 100 parts by mass of the resin composition.

The deodorant of the present invention is largely characterized in that the resin deterioration can be suppressed in a case in which the deodorant is applied to the deodorizing resin molded product. In order to further suppress the resin deterioration, it is effective to use a metal inactivator together. Examples of the metal inactivator include a methylbenzotriazole potassium salt, methylbenzotriazole, 1-hydroxybenzotriazole, benzotriazole, benzoic acid-2-hydroxyl-2-formylhydrazine, imidazole, and triazoles. Methylbenzotriazole and benzotriazole are particularly preferable. The added amounts of the metal inactivators are preferably from 0.05 to 10 parts by mass based on 100 parts by mass of the deodorant of the present invention. Particularly, the added amounts of the metal inactivators are more preferably from 0.1 to 5 parts by mass.

As a molding method of manufacturing the deodorizing resin molded product containing the deodorant or deodorant composition of the present invention, general resin molding methods such as injection molding, extrusion molding, inflation molding, and vacuum molding can be used.

The deodorizing resin molded product containing the deodorant or deodorant composition of the present invention may be utilized in various types of fields where deodorizing properties are required. For example, the deodorizing resin molded product may be used in a household electrical appliance such as an air cleaner or a refrigerator, a general domestic utensil such as a garbage can or a drainer, various types of care equipment such as a portable toilet, or a daily product.

EXAMPLES

Hereinafter, the present invention is specifically described using Examples. The present invention is not limited to the Examples. In the following description, "part(s)" and "%" are based on mass unless otherwise indicated.

1. Evaluation Method (1) Element Composition

X-ray fluorescence analysis measurement was performed using a ZSX100e type X-ray fluorescence spectrometer manufactured by Rigaku Corporation. The results were analyzed based on the amount of substance to calculate an element composition (mole) ratio of Cu/Si. A deodorant was dissolved in an acidic aqueous solution such as hydrochloric acid or nitric acid to produce a solution. The solution was subjected to ICP emission spectrometric analysis measurement using ICAP 7600 Duo manufactured by Thermo Fisher SCIENTIFIC to calculate contents (%) of Na and Cu. Furthermore, the deodorant was heated at 150° C. for 2 hours, and an amount of moisture (%) was obtained from a difference between masses before and after being heated.

(2) Bulk Specific Gravity

A sample was placed in a 100-ml measuring cylinder (volume: 138 ml) until the sample overflowed. The sample was flattened along the upper end of the measuring cylinder using a spatel or the like without compressing the sample while being vibrated, and the mass of the measuring cylinder containing the sample was then measured. The obtained value was substituted in the following formula to obtain a bulk specific gravity. The bulk specific gravity was measured at room temperature (from 20 to 30° C.).

Bulk specific gravity=$(m_S-m_C)/V$ $m_S$: Mass of measuring cylinder containing sample
$m_C$: Mass of measuring cylinder
V: Volume of measuring cylinder (3) Median Size (d50)

The median size was measured with a laser diffraction type particle size distribution meter.

The results were analyzed based on volume. A content rate % in particle size distribution is % by volume in all particles from the analyzing method. However, the density of a measured powder is constant, and the content rate % has the same meaning as that of % by mass. Specifically, the content rate % was measured with a laser diffraction type particle size distribution measuring device "MS2000" manufactured by Malvem Instruments, Inc.

(4) Specific Surface Area

The BET specific surface area was measured with "AUTOSORB-1" manufactured by Malvem Instruments, Inc.

(5) Color

The color of a sample placed in a 10-ml glass bottle was measured using a colorimeter (SZ-Σ80 colorimeter, manufactured by Nippon Denshoku Industries Co., Ltd.), and showed in Lab color space view.

(6) Deodorization Capacity 0.03 g of the dried sample was placed in a test bag (volume: 3 L) made of a vinyl alcohol-based polymer film. 3 L of a gas containing methyl mercaptan or hydrogen sulfide in high concentration (methyl mercaptan: 100 ppm, hydrogen sulfide: 200 ppm) was injected into the test bag. A residual gas concentration in the test bag after 24 hours was measured with a gas detecting tube. The deodorization capacity was represented by the volume of a gas absorbed per 1 g of the sample.

(7) Color of Molded Resin Plate

The color of a resin plate was measured using a colorimeter (SZ-Σ80 colorimeter, manufactured by Nippon Denshoku Industries Co., Ltd.), and showed in Lab color space view.

(8) Odorization of Product

A product with which the deodorant was blended was subjected to a sensory test according to the olfactions of three testers, and the product was compared with a product containing only a resin with which a deodorant was not blended. A case in which abnormal odor obviously occurred was defined as 1; a case in which abnormal odor slightly occurred was defined as 2; and a case in which no abnormal odor occurred was defined as 3.

(9) Deodorizing Performance of Molded Resin Plate

A plate having a longitudinal size of 100 mm, a vertical size of 100 mm, and a thickness of 2 mm was placed in a test bag made of a vinyl alcohol-based polymer film. 1 L of methyl mercaptan (initial concentration: 60 ppm) was injected into the test bag. A residual gas concentration in the test bag after 24 hours was measured with a gas detecting tube. The deodorizing performance was represented by the amount of a gas absorbed per plate from the measurement results.

(10) Deodorizing Performance of Binder Spread Fiber

A clothing fabric cut in 5 cm$^2$ was set in a course.

Methyl mercaptan (initial concentration: 14 ppm) or an ammonia (initial concentration: 100 ppm) gas was made to pass through the course, and a residual gas concentration was then measured with a gas detecting tube. A decrease ratio % with respect to the initial concentration was shown from the measurement results. A case in which the decrease ratio exceeded 99% was described as >99 in Table.

2. Manufacture of Deodorant

Example 1

75 g of sodium silicate No. 2 (manufactured by Aichikeisokogyo Co.) was heated to 40° C. while being stirred. The sodium silicate solution and a solution obtained by dissolving 17.8 g of copper sulfate pentahydrate and 7.3 g of sulfuric acid in 200 ml of ion exchange water were simultaneously instilled to 150 ml of ion exchange water over 1 hour so that the pH was from 6.0 to 7.5. Then, continuous stirring was performed for 1 hour for aging while a temperature of 25° C. was held, to provide a blue product. At this time, the pH of the slurry was 6.6. The slurry was filtered and washed using ion exchange water. The electrical conductivity of the filtrate after washing was 14 μS/cm. The washed cake was dried at 150° C., and then pulverized. The element composition, bulk specific gravity, median size (d50), specific surface area, deodorization capacity, and color of the obtained deodorant were measured, and the results was described in Tables 1 to 3.

Example 2

The same operation as that of Example 1 was performed except that 3.6 g of copper sulfate pentahydrate and 13.2 g of sulfuric acid were used. Then, the pH of a blue product slurry obtained by continuous stirring for 1 hour for aging while holding a temperature of 25° C. was 6.5. The electrical conductivity of the filtrate after washing was 16 μS/cm.

Example 3

The same operation as that of Example 1 was performed except that 12.5 g of copper sulfate pentahydrate and 8.8 g of sulfuric acid were used. Then, the pH of a blue product slurry obtained by continuous stirring for 1 hour for aging while holding a temperature of 25° C. was 6.3. The electrical conductivity of the filtrate after washing was 10 μS/cm.

Example 4

6,000 g of sodium silicate No. 2 (manufactured by Aichikeisokogyo Co.) was heated to 40° C. while being stirred. The sodium silicate solution and a solution obtained by dissolving 1,140 g of copper sulfate pentahydrate and 672 g of sulfuric acid in 1,600 ml of ion exchange water were simultaneously instilled to 1,200 ml of ion exchange water over 1 hour so that the pH was from 6.0 to 7.5. Then, continuous stirring was performed for 1 hour for aging while a temperature of 25° C. was held, to provide a blue product. At this time, the pH of the slurry was 6.3. The slurry was filtered and washed using ion exchange water. The electrical conductivity of the filtrate after washing was 46 μS/cm. The washed cake was dried at 150° C., and then pulverized.

Example 5

The same operation as that of Example 4 was performed except that 1,800 g of copper sulfate pentahydrate was used and sulfuric acid was not used. Then, the pH of a blue product slurry obtained by continuous stirring for 1 hour for aging while holding a temperature of 25° C. was 6.8. The electrical conductivity of the filtrate after washing was 15 μS/cm.

Example 6

The deodorant powder obtained in Example 1 and a zirconium phosphate powder were mixed at 4/1 (mass ratio).

Comparative Example 1

The same operation as that of Example 1 was performed except that 13 g of copper sulfate pentahydrate was used and sulfuric acid was not used. The pH of a blue product slurry obtained by continuous stirring for 1 hour for aging while holding a temperature of 25° C. was 7.0. The electrical conductivity of the filtrate after washing was 250 μS/cm.

Comparative Example 2

The same operation as that of Example 1 was performed except that 20.5 g of copper sulfate pentahydrate was used and sulfuric acid was not used. The pH of a blue product slurry obtained by continuous stirring for 1 hour for aging while holding a temperature of 25° C. was 7.2. The electrical conductivity of the filtrate after washing was 400 μS/cm.

Comparative Example 3

The same operation as that of Example 1 was performed except that 2.8 g of copper sulfate pentahydrate was used and sulfuric acid was not used. The pH of a blue product slurry obtained by continuous stirring for 1 hour for aging while holding a temperature of 25° C. was 6.4. The electrical conductivity of the filtrate after washing was 30 μS/cm.

Comparative Example 4

The same operation as that of Example 1 was performed except that 20.5 g of copper sulfate pentahydrate and 7 g of sulfuric acid were used, and the filtered slurry was washed using 0.05 N sulfuric acid. The pH of a blue product slurry obtained by continuous stirring for 1 hour for aging while holding a temperature of 25° C. was 6.4. The electrical conductivity of the filtrate after washing was 4 μS/cm.

TABLE 1

|  | Element composition | | |
| --- | --- | --- | --- |
|  | x | y | z |
| Example 1 | 0.016 | 0.21 | 0.15 |
| Example 2 | 0.011 | 0.07 | 0.06 |
| Example 3 | 0.010 | 0.12 | 0.20 |
| Example 4 | 0.022 | 0.17 | 0.10 |
| Example 5 | 0.021 | 0.46 | 0.30 |
| Comparative Example 1 | 0.053 | 0.25 | 0.24 |
| Comparative Example 2 | 0.059 | 0.49 | 0.30 |
| Comparative Example 3 | 0.021 | 0.05 | 0.12 |
| Comparative Example 4 | 0.001 | 0.38 | 0.40 |

TABLE 2

|  | Bulk specific gravity (g/ml) | Median diameter d50 (μm) | Specific surface area (m²/g) | Deodorization capacity (ml/g) | |
| --- | --- | --- | --- | --- | --- |
|  |  |  |  | Methyl mercaptan | Hydrogen sulfide |
| Example 1 | 0.15 | 2.6 | 380 | 62 | 173 |
| Example 2 | 0.10 | 3.8 | 420 | 31 | 104 |
| Example 3 | 0.12 | 3.7 | 450 | 45 | 144 |
| Example 4 | 0.15 | 3.4 | 390 | 53 | 170 |
| Example 5 | 0.39 | 2.6 | 400 | 65 | 194 |
| Example 6 | 0.30 | 2.2 | 380 | 47 | 147 |
| Comparative Example 1 | 0.35 | 3.0 | 410 | 10 | 139 |
| Comparative Example 2 | 0.42 | 3.1 | 480 | 61 | 158 |
| Comparative Example 3 | 0.15 | 3.8 | 400 | 21 | 81 |
| Comparative Example 4 | 0.52 | 4.6 | 400 | 62 | 171 |

TABLE 3

|  | Color | | |
| --- | --- | --- | --- |
|  | L | a | b |
| Example 1 | 83.6 | −12.3 | −11.1 |
| Example 2 | 90.1 | −8.0 | −8.4 |
| Example 3 | 85.6 | −11.9 | −10.1 |
| Example 4 | 88.7 | −11.5 | −9.1 |
| Example 5 | 81.5 | −12.5 | −12.3 |
| Example 6 | 85.6 | −9.8 | −8.3 |
| Comparative Example 1 | 86.5 | −11.6 | −10.2 |
| Comparative Example 2 | 80.2 | −12.5 | −12.8 |
| Comparative Example 3 | 89.5 | −8.5 | −8.9 |
| Comparative Example 4 | 80.6 | −13.5 | −15.8 |

The above-mentioned results show that Examples 1 to 5 which are the deodorants of the present invention have a high deodorization capacity with respect to methyl mercaptan and hydrogen sulfide, and excellent deodorizing performance with respect to sulfurous stench.

Examples 11 to 17 and Comparative Example 11

Kneading Processing to Polypropylene Resin (Production of Molded Resin Plate) 5% of each of the deodorants of Examples 1 to 5, Examples 1 to 6, and Comparative Example 1 was dry-blended with a polypropylene resin, and injection molding was performed to produce an injection-molded plate having a longitudinal size of 100 mm, a vertical size of 100 mm, and a thickness of 2 mm at a molding temperature of 220° C. 0.5% of benzotriazole was blended with Example 1 to similarly produce an injection-molded plate (Example 17). The measured results of the color value Lab of the obtained injection-molded plate, the odorization of the product, and the deodorizing properties of the molded resin plate with respect to methyl mercaptan were shown in Table 4.

TABLE 4

|  | Deodorant | Color of molded resin plate | | | Deodorizing performance of molded resin plate (μL/sheet) | Odorization of product |
| --- | --- | --- | --- | --- | --- | --- |
|  |  | L | a | b |  |  |
| Example 11 | Example 1 | 55.0 | −2.4 | 10.3 | 44 | 3 |
| Example 12 | Example 2 | 66.3 | −2.9 | 7.7 | 27 | 3 |
| Example 13 | Example 3 | 64.6 | −3.1 | 4.7 | 38 | 3 |
| Example 14 | Example 4 | 54.6 | −3.0 | 5.7 | 45 | 3 |
| Example 15 | Example 5 | 50.3 | −3.2 | 11.2 | 45 | 3 |
| Example 16 | Example 6 | 67.5 | −1.5 | 7.5 | 40 | 3 |
| Example 17 | Example 1 | 61.4 | −1.3 | 9.5 | 45 | 3 |
| Comparative Example 11 | Comparative Example 1 | 37.0 | −1.7 | 14.6 | 10 | 2 |

From the above-mentioned results, it is found that the molded resin plates in which Examples 1 to 6 and Example 1 which are the deodorants of the present invention are blended with benzotriazole have excellent deodorizing performance with respect to methyl mercaptan, a high L value as a color value, and a low b value providing less coloration and less odorization, thereby providing less resin deterioration. It is found that the resin molded plate with which Comparative Example 1 is blended has low deodorizing performance with respect to methyl mercaptan in addition to resin deterioration.

Examples 21 to 26 and Comparative Examples 21 to 24

Spreading Processing Using Acrylic Binder to Nonwoven Fabric

A polypropylene unwoven fabric having a total weight of 10 g/m² was subjected to spreading processing so that each of copper silicate deodorants of Examples 1 to 6 and Comparative Examples 1 to 4 was blended with an acrylic binder at 1:1, and the applied amount of the blended product was 5 g/m². The obtained nonwoven fabric was heated at 80° C. for 2 hours to obtain a product. The evaluation results of the odorization of the product and the deodorizing performance of the binder spread fiber were shown in Table 5.

TABLE 5

|  | Deodorant | Odorization of product | Deodorizing performance of binder spread fiber | |
|---|---|---|---|---|
|  |  |  | Methyl mercaptan (%) | Ammonia (%) |
| Example 21 | Example 1 | 3 | >99 | >99 |
| Example 22 | Example 2 | 3 | >99 | >99 |
| Example 23 | Example 3 | 3 | >99 | >99 |
| Example 24 | Example 4 | 3 | >99 | >99 |
| Example 25 | Example 5 | 3 | >99 | >99 |
| Example 26 | Example 6 | 3 | 95 | >99 |
| Comparative Example 21 | Comparative Example 1 | 2 | 79 | 98 |
| Comparative Example 22 | Comparative Example 2 | 1 | >99 | >99 |
| Comparative Example 23 | Comparative Example 3 | 3 | 61 | 89 |
| Comparative Example 24 | Comparative Example 4 | 1 | >99 | >99 |

From the above-mentioned results, it is found that the clothing fabrics obtained by subjecting Examples 1 to 6 which are the deodorants of the present invention to spreading processing have excellent deodorizing performance with respect to methyl mercaptan, and provide less odorization of the resin caused by resin deterioration.

From Examples above, it is clear that the deodorant of the present invention has excellent deodorizing performance with respect to sulfurous stench from methyl mercaptan and the like and a deodorization capacity highly maintained also after the product is processed, and provides less discoloration or abnormal odor caused by the resin deterioration of the resin product obtained by kneading and application processing.

INDUSTRIAL APPLICABILITY

A deodorant of the present invention has excellent deodorizing performance with respect to sulfurous stench from methyl mercaptan and hydrogen sulfide and the like. In a case in which various plastic products are processed, discoloration or abnormal odor caused by resin deterioration is suppressed, which causes no flaw. Therefore, by utilizing the deodorant of the present invention, excellent deodorizing properties can be applied to a fiber, a coating material, a sheet, and a resin molded product and the like, and these can be used as a deodorizing product.

The invention claimed is:

1. A deodorant comprising amorphous copper silicate represented by the following formula [1]:

$$xNa_2O.yCuO.SiO_2.zH_2O \qquad [1]$$

wherein, in formula [1], x is a positive number from 0.002 to 0.040, y is a positive number from 0.07 to 0.48, and z is a positive number from 0.02 to 0.30.

2. The deodorant according to claim 1, wherein the amorphous copper silicate has a bulk specific gravity of from 0.10 to 0.40 g/ml.

3. A deodorant composition comprising the deodorant according to claim 1.

4. A deodorizing product comprising the deodorant according to claim 1.

5. A deodorizing product comprising the deodorant composition according to claim 3.

* * * * *